United States Patent [19]
Brooks

[11] Patent Number: 4,809,709
[45] Date of Patent: Mar. 7, 1989

[54] PRESSURE-SENSING CATHETER SYSTEM WITH COMPENSATION FOR ATMOSPHERIC AND CONFIGURATION VARIATIONS

[76] Inventor: Albert E. Brooks, 1730 Ocean Oaks, Carpinteria, Calif. 93013

[21] Appl. No.: 61,946

[22] Filed: Jun. 12, 1987

[51] Int. Cl.$^4$ ............................................. A61B 5/10
[52] U.S. Cl. .................................... 128/748; 128/674; 128/780
[58] Field of Search .................... 128/672–675, 128/748, 780, 774, 782; 73/736, 747–748

[56] References Cited

U.S. PATENT DOCUMENTS

| | | | |
|---|---|---|---|
| 3,062,202 | 11/1962 | Hyman et al. | 128/674 |
| 3,437,088 | 4/1969 | Bielinski | 128/780 |
| 3,590,809 | 7/1971 | London | 128/674 |
| 3,911,902 | 10/1975 | Delpy | 128/675 |
| 4,168,703 | 9/1979 | Kenigsberg | 128/748 |
| 4,282,881 | 8/1981 | Todd et al. | 128/674 |
| 4,300,572 | 11/1981 | Knighton | 128/674 |
| 4,601,706 | 7/1986 | Aillon | 128/673 X |
| 4,621,646 | 11/1986 | Bryant | 128/673 X |
| 4,672,974 | 6/1987 | Lee | 128/673 |

Primary Examiner—Edward M. Coven
Assistant Examiner—Angela D. Sykes
Attorney, Agent, or Firm—Donald D. Mon

[57] ABSTRACT

A catheter incorporates a pair of flexible conduits which are structurally united over a major portion of their length where bending is likely to occur during use so they both undergo the same deformations. Each conduit contains an aqueous column that terminates at a meniscus. The meniscus interfaces directly with a column of a different liquid which is insoluble in and immiscible with the liquid in the aqueous column. One of the conduits is a pressure responsive conduit and the other is a stagnant conduit.

9 Claims, 1 Drawing Sheet

U.S. Patent    Mar. 7, 1989    4,809,709
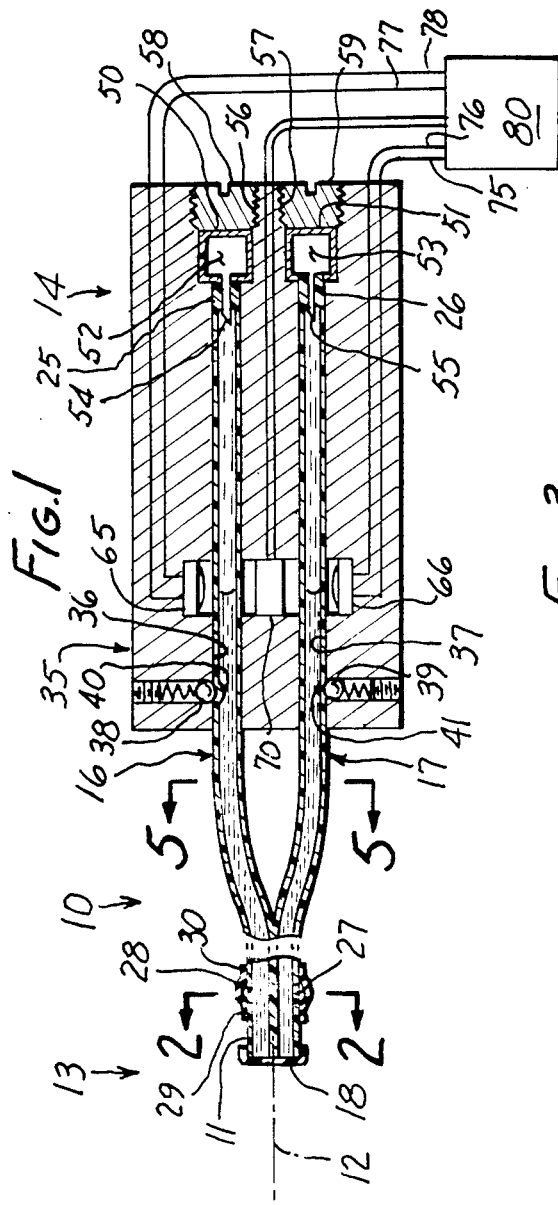
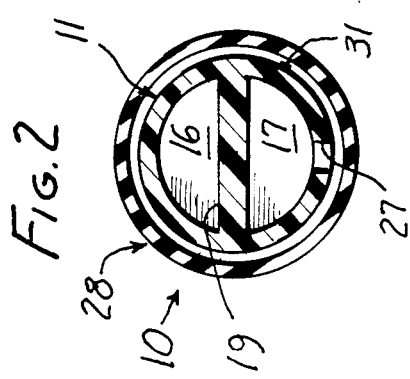
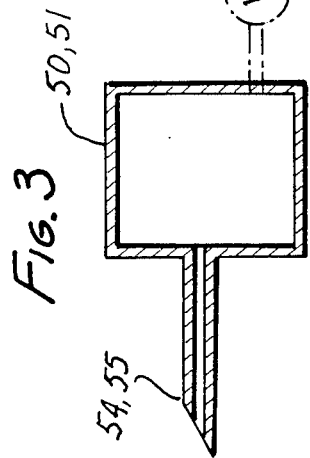
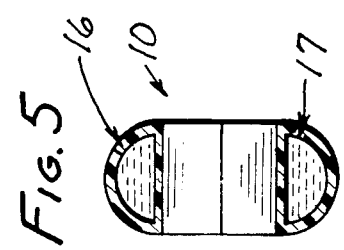
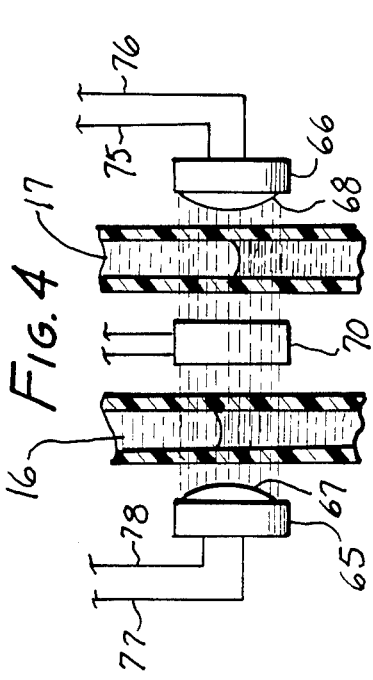

PRESSURE-SENSING CATHETER SYSTEM WITH COMPENSATION FOR ATMOSPHERIC AND CONFIGURATION VARIATIONS

FIELD OF THE INVENTION

This invention relates to catheters which are used to sense pressure in an internal region, for example in coronary arteries, and in the lower urinary tract.

BACKGROUND OF THE INVENTION

Flexible catheters are inserted into the body in order to measure fluid pressure in regions of interest. Catheters are inserted into the coronary arteries and into the lower urinary tract for this purpose, and are useful in other procedures also. At the distal end or somewhere along the length of the catheter, or at both places, it is known to incorporate pressure-responsive electronic sensors. These require that conductive leads extend along the catheter structure. In the course of measurement, electrical currents are introduced through them into regions of the body where stray electrical fields are considered by many to be undesirable. These devices are relatively expensive, and must be individually calibrated.

Manometer techniques have also been used for such measurements. These have the considerable advantage that they do not require the introduction of electrical currents into the body and accordingly are potentially safer. Also they are potentially much less expensive, because they are little more than small tubes which carry a liquid column whose height is proportional to the pressure being measured.

However, fluid column techniques do have problems of their own. One is that a major portion of their length will often be flexed in various and varying directions during a procedure. A bend in a flexible tube will result in a reduction of the contained volume in the bent region, which will cause the displacement of some of the liquid which it holds. This displaced fluid will be read as a change in pressure because the meniscus will move, so that there is a latent inaccuracy in measurements when flexible tubing is used in a manometer system.

Yet another important variable in measurements made with known manometric techniques is the "station elevation" (atmospheric pressure) of the community where the measurement is done. Atmospheric pressure in Denver, Colo., will always be importantly different from the atmospheric pressure at sea level. This can lead to inconsistencies in readings of the same instrument from locale to locale.

It is an object of this invention to provide a fluid-coupled catheter capable of providing a fluid pressure indication outside of the body which is inherently compensated for atmospheric pressure differences and variations, and for configuration variations such as are caused by changes in the volume of the flexible tubing used for the catheter by its being bent and unbent during use, such as may occur when a recumbent patient sits up or a standing patient bends over.

BRIEF DESCRIPTION OF THE INVENTION

A catheter according to this invention incorporates a pair of flexible conduits which are structurally united over a major portion of their length where bending is likely to occur during use so they both undergo the same deformations. Each conduit contains an aqueous column that terminates at a meniscus. This meniscus interfaces directly with a column of a different liquid which is insoluble in and immiscible with the liquid in the aqueous column. The transmissivities of the aqueous column and of the other column to radiation such as infrared or visible light, are different from one another.

The first of said conduits is a "pressure-responsive" conduit. It terminates at a port covered by a flexible impermeable membrane which transmits pressure in the region being sensed to the respective aqueous column. In turn, variations in the pressure being measured will cause the aqueous column to move in the conduit in the sense of shifting, thereby moving the miniscus, which is located at a substantial distance from the port.

The second conduit is denoted as "stagnant" conduit. It extends along the pressure-responsive conduit, being united therewith for most of their flexible length. Its distal end is sealed. It is not sensitive to pressure being measured. It does, however, have the same general dimensions as the flexible part of the pressure-responsive conduit.

Sensor means is provided for each of the meniscuses, responsive to the position of the meniscuses. Variations shared by both conduits will be sensed by the sensors respective to both conduits. Variations of sensed pressure will be sensed only by the sensor respective to the pressure-responsive conduit. Their difference is a simple and accurate measurement of the pressure, compensated for other variables such as bending, changes in elevation, and the like.

Gas bias means is provided for each of the conduits at their proximal end. Each said bias means exerts a bias force on the respective immiscible column. These gas bias means preferably have the same volume and pressure, and the pressure may conveniently be that of the "station", so as to correlate the readings with the existing atmospheric conditions rather than with some arbitrary standard. Because the flexible length of both aqueous columns are substantially equal, this provides an automatic zero for the system. The volume of confined gas acts as a spring or cushion opposing the pressure being measured, through the respective column, so the positions of the meniscuses become an accurate measurement of the conditions to which they are responsive.

According to a preferred but optional feature of the invention, both conduits may initially be filled and sealed without gas in them. This makes for optimum storage and good shelf life. When the cathether is to be used, the proximal ends are punctured to connect the tubes to a source of gas.

The above and other features of this invention will be fully understood from the following detailed description and the accompanying drawings, in which:

BRIEF DESCRIPTION OF THE DRAWINGS

FIG. 1 is an axial cross-section, partly in schematic notation, showing the presently-preferred embodiment of the invention;

FIG. 2 is a cross-section taken at line 2—2 in FIG. 1;

FIG. 3 is a fragmentary schematic view of an alternate gas source;

FIG. 4 is a fragmentary enlarged vignette from FIG. 1 better illustrating the measurement concept of this invention; and FIG. 5 is a cross-section taken at line 5—5 in FIG. 1

DETAILED DESCRIPTION OF THE INVENTION

The presently-preferred embodiment of a catheter 10 according to the invention is shown in FIG. 1. The dimensions are considerably enlarged and exaggerated in some parts for purposes of illustration. For example, the diameter of the catheter over most of its length is no more than about 1/16 inch. The catheter is conveniently made as a flexible extrusion. It has a circular outside wall 11, an axis 12 of length, a distal end 13 and a proximal end 14.

The conduitry which is the subject of this invention could be made with two separate lengths of tubing united by a binding, a wrapping, or a cast-in-place potting. It is more convenient to form conduitry as part of a continuous extrusion, with the conduits sharing a common wall or walls. This can materially reduce the outer diameter, or enable a larger number of conduits to be provided within the diameter of the tubing, as will later become apparent.

As best shown in FIG. 2, a stagnant conduit 16 and a pressure-responsive conduit 17 each with its own lumen are formed inside wall 11. An end seal 18 at the distal end closes both conduits. A common wall 19 is shared by the two conduits. While the cross-section for the conduits is basically sector-shaped, other cross-sections are equally useful. However, the material and its dimensions should be selected so that the walls of the conduits generally bend together without wrinkling or other uncontrolled distortions which might make the volumes of the conduits substantially unequal. These conduits have a small cross-section, and the pressures measured are rarely more than a few inches of water. The meniscuses usually will not move more than about 3/16 inch over the total range. This shows how important the compensation for volume change can be.

Near their proximal ends, the conduits are separated by a knife cut through common wall 19. Conduits 16 and 17 are capped by plugs 25, 26. Stagnant conduit 16 is initially totally closed. Wall 11 is pierced by port 27 which enters into the pressure responsive conduit.

A fully peripheral membrane 28 extends around the catheter. Peripheral seals 29, 30, one on each axial side of port 27, seal the membrane to the catheter at its edges. The membrane is flexible and thin. While it is initially shaped as shown to provide some clearance 31 around the catheter, this is principally attained by compressing the length of a tubular membrane before sealing its edges. The function of the membrane is to transfer the outside pressure to the port but without exerting forces of its own. An increase in outside pressure will squeeze the membrane toward the catheter, as will later be described.

The catheter and the membrane will be made of any suitable material not antagonistic to human tissue or to the fluids whose pressure is to be measured. Organic plastic materials such as polypropylene, polyvinyl chloride, or silicone rubber are suitable for the catheter. The membrane will usually be made of silicone rubber.

A receptacle 35 is provided to receive the proximal ends of the conduits. Socket 36 receives the proximal end of the stagnant conduit. Socket 37 receives the proximal end of the pressure-responsive conduit. Spring loaded ball detents 38, 39 retain the conduits. If desired, dimples 40, 41 can be formed to locate the conduits at the detents.

Both of the conduits are initially closed by their respective plugs. The plugs can be pierced. During storage they preserve the contents of the conduits, which are best filled completely with the liquids to the exclusion of gases. Gases can be contained in them, and the contained gases can provide the gaseous bias means needed for the operation of the system. However, in storage or in handling it is possible for the gas to be shaken into the immiscible column, and perhaps beyond it into the aqueous column. Then the meniscus is not as readable, and the bias function of the gas may be compromised.

Instead, rigid containers 50, 51, each having an internal chamber 52, 53 and a piercing type hollow needle 54, 55 are provided. In the preferred embodiment these containers are merely left in the atmosphere so that the chamber is filled with air at station pressure. The volume of the cavity plus that of the hollow needle is the same for both conduits. The containers are fitted in sinks 56, 57 and retained in them by threaded plugs 58, 59. When the conduits are pressed into their sockets, they are pierced by the needles, and the contained air becomes a bias means against the columns. It is possible to use the needles themselves for the gas volume, without the chamber, the needles themselves constituting sufficient chamber for air.

FIG. 3 shows that if instead of atmospheric pressure, some other gas pressure is preferred, a pressure source 60 and valve 61 can be provided for that purpose. Perhaps some other valving at the nedle end will be needed. However, the arrangement of FIG. 3 will rarely be used.

As best shown in FIGS. 1 and 4, each conduit is provided with a sensor 65, 66, with focusing lenses 67, 68. The walls of the conduits in the range where the meniscuses will stand are transparent to radiation of the type used to observe the position of the meniscuses. A radiation source 70 is provided between the two conduits, and its output radiation passes through the conduits and columns to be received by the sensors. The presently preferred radiation source is a light-emitting diode (LED), emitting visible light. Suitable detectors (sensors) will be receptive to the wavelengths emitted by the source and passed by the conduit walls and the columns.

Because the columns in each conduit are differently transmissive, the meniscus represents a boundary between a region of greater transmissivity and lesser transmissivity. The less transmissive column acts as a "shutter", which may obstruct all or only a portion of the light. Preferably it will be colored with an acceptable coloring agent such as a dark food dye. This will improve the contrast. Accordingly, if the aqueous column is the lesser transmissive of the two, the total radiation received by the sensor will be less when the pressure is greater, and greater when the pressure is lesser. The output of the sensors can be conducted by leads 75, 76, 77, 78 to circuitry 80.

Circuitry 80 reads out the position of both meniscuses, and their difference can be calculated by subtracting them. The difference is a unique function of the measured pressure. Any desired compensation for other variables such as temperature, can be incorporated in the circuitry. This forms no part of the instant invention.

Should more than two conduits be useful to provide more than one place to measure pressure, for example, the extrusions can be modified to provide them, and ports can pierce the wall to connect the other conduits to the outside of the tube, where still another membrane will be placed. This enables pressure response to be measured at more than one place along the catheter, still maintaining the correlation with the stagnant conduit. Alternately, more than two conduits can be provided as bound-together individual tubes.

It is advantaegous to have as flat a meniscus as possible. When silicone oil, rather than mineral oil, is used for the immiscible column, it appears to wet the wall of the conduit so as to result in a flatter meniscus, and is therefore to be preferred.

The term "column" as used herein is not limited in the sense of an upright or vertical structure. It is intended to mean a length of confined liquid, whatever its orientation.

A bend in the conduits will reduce the lumen volume and move the meniscus to the right in FIG. 1. A straightening of the conduits from a bent configuration will move the meniscus to the left. This response occurs in both tubes simultaneously, while meniscus movement in the response to changes in measured pressure occurs only in the pressure-responsive conduit. Therefore the "environmental" changes are compensated by measuring the difference between the two meniscus positions. This provides an automatic zero and running compensation in an elegantly simple device.

This invention is not to be limited to the embodiments shown in the drawings and described in the description, which are given by way of example and not of limitation, but only in accordance with the scope of the appended claims.

I claim:

1. A catheter for measuring pressures in internal regions, said catheter comprising a first stagnant conduit and a second pressure-responsive conduit, both of said conduits having a boundary wall, are flexible and have a lumen, said lumens having a proximal end and a distal end, said tubes being coextensive, parallel, united together, and having substantially identical cross-sections for a major portion of their length, a port through said boundary wall of said pressure responsive conduit into its respective lumen, a flexible impermeable membrane covering said port and transferring the pressure outside of the cathether to said port and thereby to its respective said lumen, the distal end of the lumen of said stagnant conduit being closed, an aqueous liquid column in both of said lumens extending from their distal ends, and an immiscible liquid column contiguous with each of said aqueous columns forming a meniscus interface therewith; and gas bias means communicable with said immiscible liquid columns at said proximal end of said lumens, whereby the location of said meniscuses and the relative location of both meniscuses provide an indication of the pressure in said region independent of bending distortions of the cathether.

2. A catheter according to claim 1 in which coloring material is added to said aqueous columns.

3. A catheter according to claim 1 in which said gas bias means is a confined volume of gas in fluid communication with each of said immiscible columns.

4. A catheter according to claim 3 in which both conduits are closed at their proximal ends, without gas in said lumens, and in which a hollow piercing needle is provided to pierce said pressure responsive conduit to provide said gas bias means to said immiscible columns.

5. A catheter according to claim 4 in which said piercing needle is coupled to a fixed volume gas-containing chamber.

6. In combination:
   a catheter for measuring pressures in internal regions, said catheter comprising a first stagnant conduit and a second pressure responsive conduit, both of said conduits having a boundary wall, are flexible and have a lumen, said lumens having a proximal end and a distal end, said tubes being coextensive, parallel, united together, and having substantially identical cross-sections for a major portion of their length, a port through said boundary wall of said pressure responsive conduit into its respective lumen, a flexible impermeable membrane covering said port and transferring the pressure outside of the catheter to said port and thereby to its respective said lumen, the distal end of the lumen of said stagnant conduit being closed, an aqueous liquid column in both of said lumens extending from their distal ends, and an immiscible liquid column contiguous with each of said aqueous columns forming a meniscus interface therewith; and gas bias means communicable with said immiscible liquid columns at said proximal end of said lumens, whereby the location of one of said meniscuses and the relative location of both meniscuses provide an indication of the pressure in said region independent of bending distortions of the catheter;
   sensor means for sensing the location of each meniscus; and
   means to determine the observed pressure as a function of the location of the meniscus in the pressure responsive conduit and of the difference in locations of the two meniscuses.

7. A combination according to claim 6 in which said sensor means comprises a radiation source at a side of each conduit, and a detector means at the opposite side of each conduit from said radiation source, the conduits being lighttransmissive at this location, and the transmission properties of the columns being different, whereby the location of each meniscus can be calculated from the proportion of radiation transmitted through the conduits.

8. A combination according to claim 6 in which a receptacle includes a socket for each conduit to receive said conduit, each said socket including piercing needle means to pierce a respective conduit, thereby to provide said gas bias means, and in which said sensor means is incorporated in said receptacle.

9. A combination according to claim 8 in which said sensor means comprises a radiation source, and a detector means on the opposite side of each conduit from said radiation source, the conduits being light transmissive at this location, and the transmissive properties of the columns being different, whereby the location of each meniscus can be calculated from the proportion of radiation transmitted through the conduits.

* * * * *